United States Patent [19]
Adrey et al.

[11] Patent Number: 5,021,062
[45] Date of Patent: Jun. 4, 1991

[54] ACETABULAR CUP ASSEMBLY

[76] Inventors: José Adrey, 43, Faubourg St. Jaumes, 34000 Montpellier; Daniel Berteaux, 64bis, rue des Fossés, 45400 Fleury les Aubrais; Christian Goalard, 43, Faubourg St. Jaumes, 34000 Montpellier; Alain Gueret, 29-31 rue Thiers, 88000 Epinal; Georges Hamon, rue Henri Barbusse, 59880 Saint Saulve; Christian Nourissat, 75 rue Général Giraud, 42308 Roannes Cedex, all of France

[21] Appl. No.: 531,268

[22] Filed: May 31, 1990

[30] Foreign Application Priority Data

Jun. 21, 1989 [FR] France ............................... 89 08289

[51] Int. Cl.$^5$ .............................................. A61F 2/32
[52] U.S. Cl. ......................................... 623/22; 623/16
[58] Field of Search ................... 623/22, 23, 18, 16

[56] References Cited

U.S. PATENT DOCUMENTS

| | | | |
|---|---|---|---|
| 4,563,778 | 1/1986 | Roche et al. | 623/22 |
| 4,792,337 | 12/1988 | Muller | 623/22 |
| 4,828,565 | 5/1989 | Duthoit et al. | 623/22 |
| 4,840,632 | 6/1989 | Kampner | 623/22 |
| 4,871,368 | 10/1989 | Wagner | 623/22 |
| 4,955,325 | 9/1990 | Zarnowski et al. | 623/22 |

FOREIGN PATENT DOCUMENTS

| | | |
|---|---|---|
| 0120595 | 10/1984 | European Pat. Off. . |
| 0265712 | 5/1988 | European Pat. Off. . |
| 663893 | 1/1988 | Switzerland . |
| 668180 | 12/1988 | Switzerland . |

Primary Examiner—Ronald Frinks
Attorney, Agent, or Firm—Peter C. Richardson; Lawrence C. Akers; Raymond W. Augustin

[57] ABSTRACT

An acetabular prosthesis assembly for implantation into a prepared acetabulum has a generally hemispherically-shaped cup. The cup has a substantially hemispherically-shaped inner surface and a substantially hemispherically-shaped outer surface defining a wall therebetween. The wall has a plurality of generally circular apertures therein for receiving a bone screw. The wall surrounding each aperture has a bevelled surface extending toward the outer surface followed by a generally cylindrical surface extending from the bevelled surface to the outer surface of the cup. The generally cylindrical surface of each aperture is threaded with threads of predetermined diameter and pitch. A bone screw has a first screw thread having a pitch and diameter for engagement with the thread of the cylindrical surface on the cup and a second screw thread having a major diameter and a pitch greater than the predetermined diameter and pitch of the cylindrical surface. A plastic insert for attachment to the inner surface of the cup is provided.

7 Claims, 3 Drawing Sheets

ACETABULAR CUP ASSEMBLY

BACKGROUND OF THE INVENTION

1. Field of the Invention

The present invention relates to an acetabular cup assembly for a hip prosthesis. More particularly, this invention relates to a bone screw for fixing the acetabular cup to the acetabulum.

2. Description of the Prior Art

Known total hip prostheses include prosthetic femoral components and acetabular cup assemblies in which a spherical head integral with the femoral component can rotate freely in a spherical cavity in the acetabular cup. This allows a prosthetic assembly to replace the normal articulation of the hip.

The prosthetic acetabular cups of these known prostheses are generally fastened in the patient's iliac bone either directly by being screwed into the acetabulum, or through the use of bone screws, or indirectly, by means of an acrylic bone cement.

Examples of acetabular cups which are threaded are shown in U.S Pat. Nos. 4,062,891, 4,795,469, 4,813,961 and 4,822,367. In these acetabular cups an external screw thread is made of metal and its implantation requires prior preparatory work on a large area of a healthy part of the iliac bone by tapping the bone. This step risks weakening this bone and thus compromises the seat of the prosthetic acetabulum.

With bone cement, an acetabulum made of a polyolefin, for example polyethylene, and comprising a number of cavities or external protuberances intended to ensure its fixation, must be introduced immediately after the acrylic bone cement has been applied. The cup must be firmly maintained under pressure while the cement polymerizes in situ. This involves delicate handling of the cup and extends the duration of the operation. This process also produces the setting of a intermediate layer of cement which is never fully compatible with the bony tissue.

U.S. Pat. Nos. 4,792,337 and 4,871,368 are examples of the use of bone screws in the fixation of an acetabular cup prosthesis to a prepared acetabulum. The use of bone screws has been found to overcome many of the problems of the prior art fixation systems. However, it has been found that an acetabular cup fixed only with bone screws can subside into the cavity or part of the cavity formed in the acetabulum thus causing the threaded coupling to loosen at least in certain areas.

SUMMARY OF THE INVENTION

It is an object of the invention to provide an improved prosthetic acetabulum for a total hip prosthesis which avoids the drawbacks of previously used acetabular cups.

It is a further object of the invention to provide a bone screw that can be used with an acetabular cup having threaded apertures therein which screw enables the cup of the prosthesis to be locked to the bone screws.

These objects are achieved in the prosthetic hip acetabulum according to the present invention which has the form of a metallic cup comprising inner and outer surfaces forming concentric hemispheres defining a wall therebetween. The cup is characterized by a smooth outer surface and is provided with threaded aperture comprising an axially oriented aperture and lateral apertures oriented around the spherical surface at various angles with respect to the plane defined by the open end of the cup. The acetabular cup also comprises locking elements adjacent its open circular extremity.

The smooth outer surface of the acetabular cup of the present invention can easily be covered in a known manner by a layer of hydroxyapatite because of its metallic nature and the absence of any protrusions. The hydroxyapatite facilitates the cups compatibility with the bony tissue and encourages bone ingrowth.

Fastening the acetabular cup in the iliac bone is accomplished without cement by one or a plurality of unique bone screws introduced into the lateral apertures provided in the walls of the acetabular cup. This system permits the acetabular cup to be completely inserted and secured in the osseous cavity. Good initial fixation is especially necessary when a cup is covered with hydroxyapatite, and the system of the present invention minimizes the prior work of preparing the iliac bone to receive the prosthetic element.

Each lateral aperture, preferably circular in shape, is provided with a counterbore intended to ensure proper effacement or seating of the head of the bone screw or spikes inside the acetabular cup. Each aperture is threaded, which thread is intended to cooperate with a first thread form on the bone screw in order to make the acetabular cup integral with the screw or spikes after being anchored in the acetabulum.

The axial aperture on the acetabular cup of the present invention has two purposes: (a) to facilitate placement of the prosthetic cup by the surgeon to permit its temporary fixation, for example by threading it onto an axial manipulating rod, and (b) to serve as a counterbore for the head of an insert of plastic material.

Finally, the acetabular cup of the present invention comprises, adjacent its open circular extremity, internal locking elements. The locking elements may be in the form of a circular rib and include a cylindrical surface centered around the same axis as the central axis of the spherical cup. This cylindrical surface is provided with locking receptacles or recesses. In a preferred embodiment, these locking receptacles or recesses are distributed symmetrically in relation to the central axis of the cup and are in the form of axial recesses formed by drilling a bore in the wall of the cylindrical surface.

Given that the acetabular cup must cooperate with the spherical head of the femoral element of the prosthesis and that it is extremely important for these two elements to be able to pivot freely in relation to one another without being damaged, provision is made for introducing an insert made of a plastic material, such as polyethylene, inside the cavity of the acetabular cup.

This insert is normally cup-shaped and has an external surface which conforms to the inner surface of the cup and has an internal surface in the form of a spherical cup generally concentric with its external surface. The inner surface is intended to cooperate with the spherical head of the femoral element of the prosthesis. The insert has a cylindrical axial protrusion which cooperates with the axial apertures of the acetabular cup so as to fit therein. It also has a circular flange and anti-rotation lugs located externally and near its open circular extremity, which lugs are intended to cooperate with the internal locking recesses of the acetabular cup so that the insert may be snap fit therein with the lugs preventing rotation.

This plastic insert is interposed between the metal acetabular cup and the spherical head (usually metal or ceramic) of the femoral component of the prosthesis to protect the head from being in direct contact with the metal inner surface of the cup and the heads of the fastening screws or spikes therein. The insert also acts as a bearing to ensure universal rotation with minimal friction. The insert is preferably made of plastic material known for its low friction coefficient, such as polypropylene or polyethylene.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
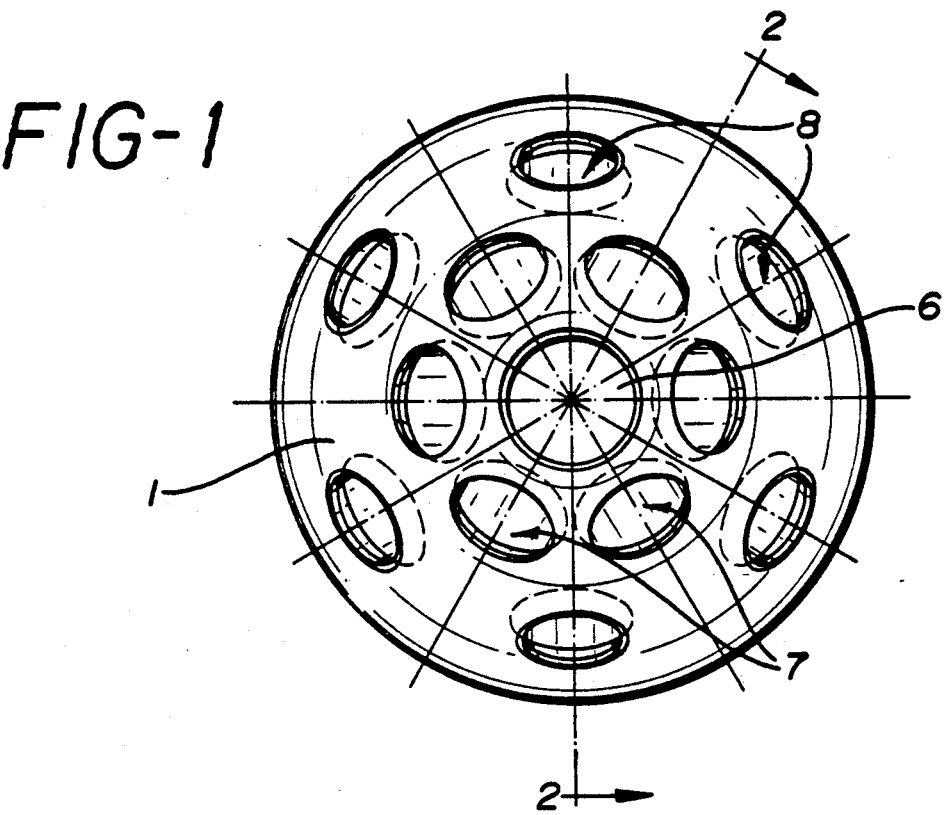
FIG. 1 is a plan view of the acetabular cup of the present invention.
Figure 2:
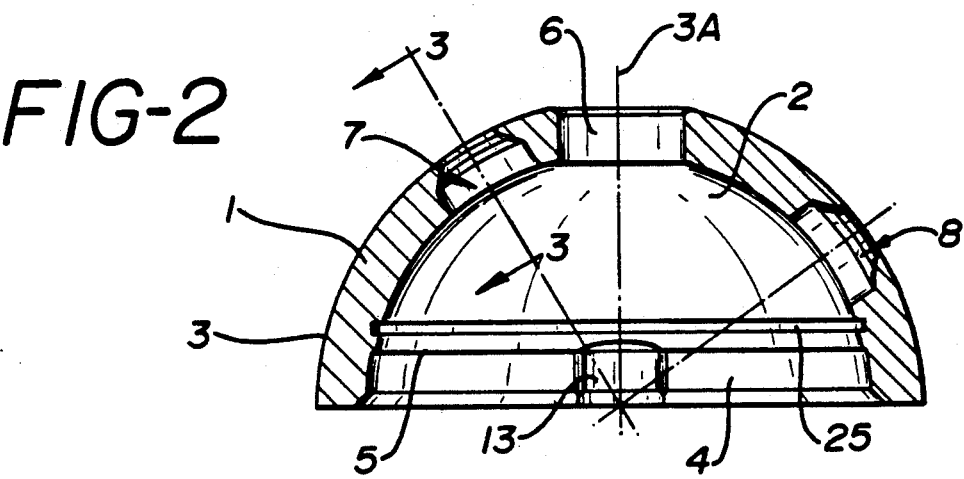
FIG. 2 is a cross-sectional view along line 2—2 of FIG. 1.

Referring to FIGS. 1 and 2, the acetabular cup of the invention, generally denoted with the reference number 1, appears in the form of a cup-shaped shell whose inner surface 2 and outer surface 3 are in the form of spherical cups concentric about axis 3A. Preferred cup 1 has an extension in the form of a cylindrical locking rim 4 concentric with axis 3A. Cup 1 terminates in an open circular end 5.

In the preferred embodiment, cup 1 has a threaded axial opening or aperture 6 and its spherical surfaces 2, 3 comprise two rows of holes, each having six cylindrical apertures 7, 8, symmetrically distributed along two concentric circles in a staggered arrangement. Of course, the distribution of apertures 7 and 8 may be in any arrangement as long as the surgeon is provided sufficient flexibility for fixation upon implantation.

In the preferred embodiment of FIGS. 1 and 2, the angles formed by the axes of the first row of apertures and the second row of holes 8, in relation to the plane of spherical cups 2, 3 defined by open end 5, are approximately 60° for holes 7 and approximately 35° for holes 8. This relationship of aperture rows results in the first row of apertures 7 being oriented in relation to the polar axis 3A of the cup at an angle of approximately 30° and those of the holes 8 of the second row at an angle of approximately 55°. Such angles, when combined with a staggered arrangement of the two rows of apertures, facilitate the implantation and fixation of the prosthesis in the patient by the surgeon.

Figure 3:
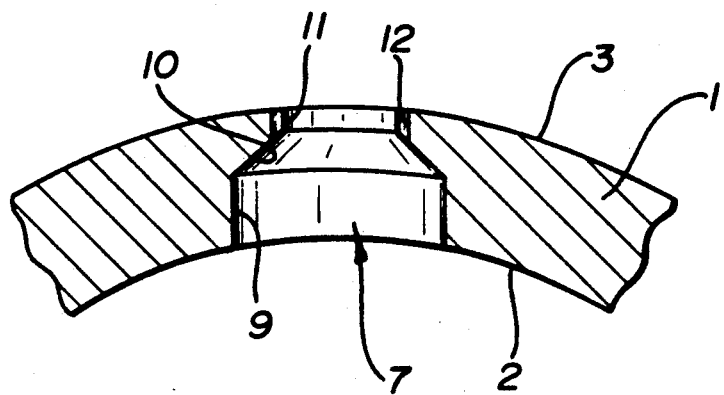
FIG. 3 is a cross-sectional view along line 3—3 of FIG. 2.

Referring to FIG. 3, each hole 7, 8 has a preferred construction comprising, proceeding from the inner surface 2 of cup 1 in the direction of outer surface 3, a cylindrical counterbore 9 intended to receive the beveled head of a fastening screw (described hereinafter), a bevel 10 serving to seat this head and a cylindrical extension 11 having a diameter smaller than that of the counterbore 9. Extension 11 has a thickness sufficient to accommodate at least one or two threads 12 which extend from inner surface 2 and emerge on outer wall 3 of the cup. Threads 12 cooperate with a corresponding thread on the screw and spikes to lock it in the aperture in question and thus lock the screw or spikes to cup 1.

On its inner surface 2, locking rim 4 of preferred acetabular cup 1 also has a circular locking groove 25 located near its open circular extremity 5. Preferred cylindrical locking surface 4 also comprises, as shown in FIG. 2, locking recesses or receptacles symmetrically arranged about the axis of the cup. These recesses consist of a series of bores, 13 which extend parallel to the axis of the acetabular cup which bores are drilled at regular intervals in the inner circular wall so as to form guide grooves. Acetabular cup 1 is preferably made of metallic material, particularly a titanium alloy, and is advantageously covered along its entire outer surface 3 with a covering layer known to be absorbed in blood environment, such as a coat of hydroxyapatite.

Figure 5:
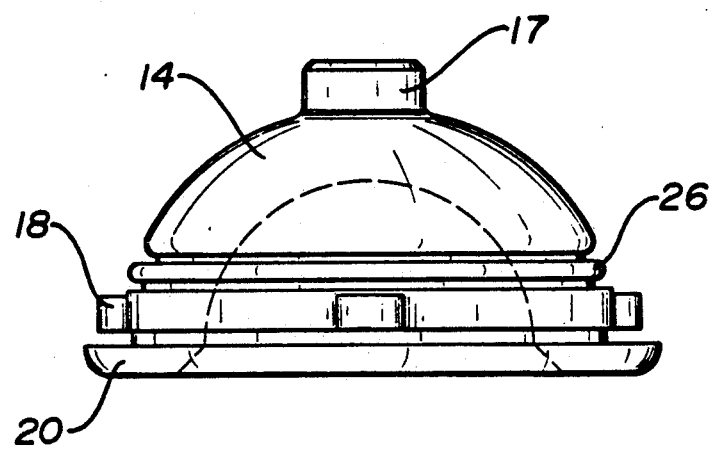
FIG. 5 is a side view of the insert shown in FIG. 4.
Figure 4:
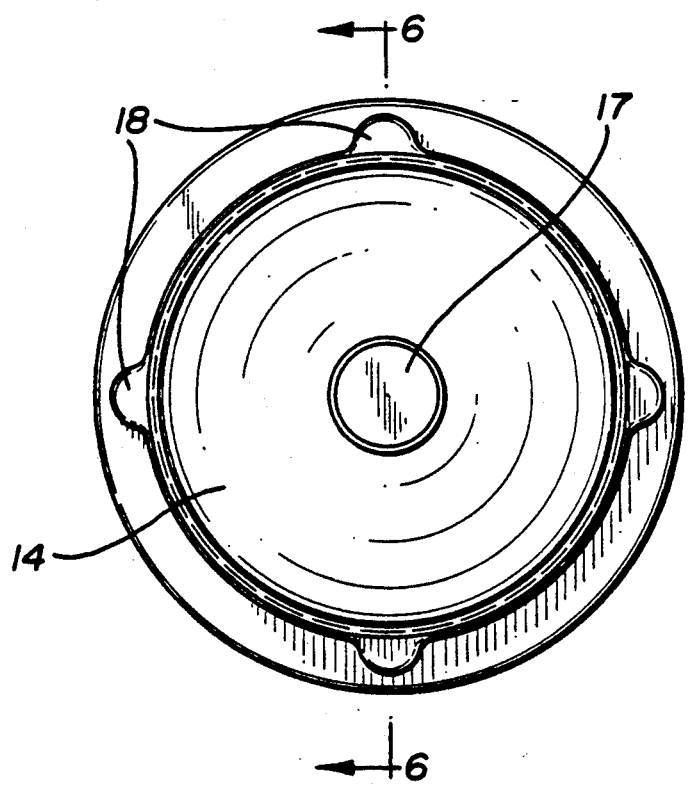
FIG. 4 is a plan view of the plastic insert to be used with the acetabular cup of the present invention.
Figure 6:
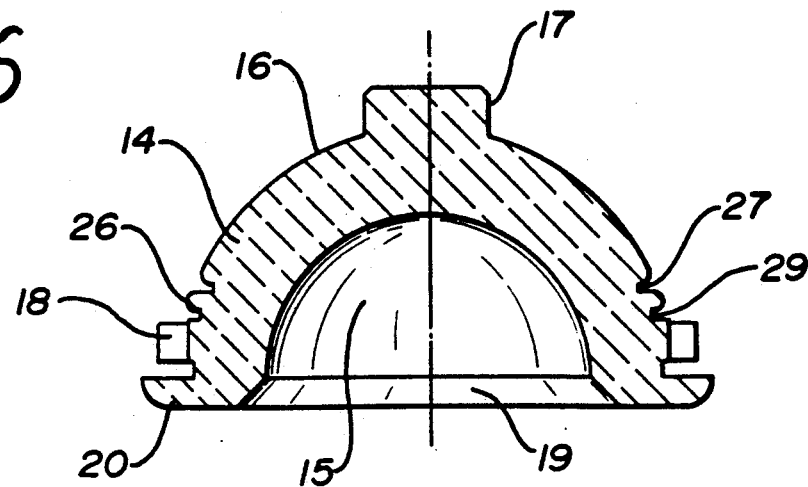
FIG. 6 is a cross-sectional view of the insert shown in FIG. 4 along line 6—6.

Referring to FIGS. 4 to 6, there is shown a plastic insert 14 for use with acetabular cup of the present invention. Insert 14 has the shape of a cup whose inner and outer walls 15 and 16, respectfully, are concentric spherical cups. Inner wall 15 cooperates with the spherical head of the femoral element of the prosthesis (not shown), and outer wall 16 conforms precisely to the inner wall 2 of acetabular cup 1. Insert 14 comprises, on the outside, a cylindrical axial protrusion 17 intended to be accommodated in axial opening 6 of cup 1 and, near an open circular end 19 of the insert, a circular flange 26 delimited by two likewise circular recesses 27 and 29. Insert 14 also includes projections in the form of antirotation lugs 18, at regular intervals.

Insert 14 may also include a corresponding collar 20 at its open end 19 which collar 20 extends outwardly so as to cover the edge of the wall formed between surfaces 2 and 3 of acetabular cup 1 when insert 14 is introduced into cup 1. The insert 14, when introduced inside acetabular cup 1, snaps onto the latter through cooperation of the flange 26 with groove 25 and it is prevented from rotation because of the cooperation of lugs 18 which are received in bores 13.

Figure 7:
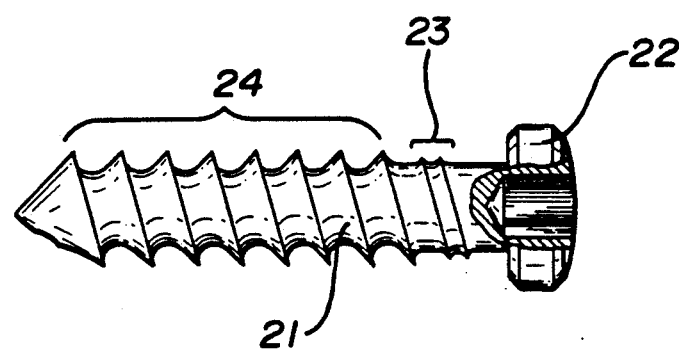
FIG. 7 is a side view of the double-threaded bone screw of the present invention partially in cross-section.
Figure 8:
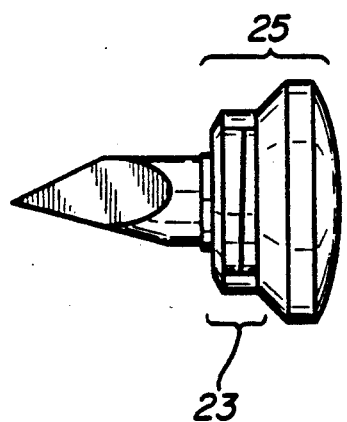
FIG. 8 is a side view of a threaded spike which may be used in lieu of the bone screw represented in FIG. 7.

The means used to fasten the cup 1 in the cavity of the patient's iliac bone are preferably the bone screw shown in FIG. 7 or the spike represented in FIG. 8. These screws 21 comprise two successive threads of different pitch, namely, starting from the head 22 of the screw, a first thread 23 whose smaller pitch cooperates with the threads on threaded extension 11 of acetabular cup 1. Specifically, thread 12 of FIG. 3 is designed to engage thread 23 on bone screw 21. A second thread 24 whose pitch is larger than the pitch of thread 23 is intended to ensure fixation in the patient's bone.

In the preferred embodiment, the major diameter of thread 24 is greater than the major diameter of screw thread 23. However, the minor diameter of threads 24 is such that contact with the peaks of threads 12 of apertures 7, 8 is avoided. In order for screw 21 to be inserted in apertures 7, 8 it is necessary that the pitch and shape of threads 24 be such that two adjacent peaks of threads 24 can pass over two adjacent peaks of thread 12 without engagement therewith. Of course, when threads 23 contact threads 12, tight engagement occurs locking screw 21 to cup 1. This locking prevents subsidence of cup 1 should a part of the iliac bone recede due to inadequate stress transfer. The cup would still be held in place as long as threads 24 of screws 21 are firmly anchored in bone.

In lieu of the screw 21, a spike 25, having a single thread 23 cooperating with the threaded extension of acetabular cup 1 and a sharp end, as shown in FIG. 8, may be used to fasten the cup 1 to the patient's bone.

The acetabulum according to the invention is of especially simple construction and has the great merit of being able to be covered externally with a coating absorbable in the environment of the blood, which facilitates its compatibility with the surrounding tissues of the bone. It also avoids the use of any cement, the setting and polymerization of which are always time-consuming and delicate and often give rise to postoperative problems.

While two examples of the present invention have been described, it is obvious that many changes and modifications may be made thereunto, without departing from the spirit and scope of the invention.

We claim:

1. An acetabular cup for use with a bone screw comprising:
   a generally hemispherically shaped cup having a substantially hemispherically-shaped inner surface and a substantially hemispherically-shaped outer surface defining a wall therebetween, said wall having a plurality of generally circular apertures therein for accommodating the bone screw, the wall surrounding each aperture having a bevelled surface extending toward said outer surface followed by a generally cylindrical surface extending from said bevelled surface to said outer surface of said cup, said generally cylindrical surface being threaded with threads of predetermined diameter and pitch.

2. The acetabular cup as set forth in claim 1 wherein the cup is made of a titanium alloy.

3. The acetabular cup as set forth in claim 1 wherein said outer surface is smooth and covered with a coating of hydroxyapatite.

4. The acetabular cup as set forth in claim 1 wherein said plurality of circular apertures comprises one threaded circular axial aperture and a plurality of laterally oriented threaded circular apertures located symmetrically in relation to a polar axis of the cup.

5. The acetabular cup as set forth in claim 4 wherein the lateral circular apertures form two rows, each having a plurality of apertures each symmetrically distributed in a staggered arrangement in relation to one another, the angles of the first row of apertures forming, with respect to said axis of the cup a different angle from the second row of apertures.

6. The acetabular cup as set forth in claim 5 wherein the angles of the first row of apertures is oriented, in relation to said axis of the cup at an angle of approximately 30° and those of the second row an angle of approximately 55°.

7. An acetabular prosthesis assembly for implantation into a prepared acetabulum comprising:
   a generally hemispherically shaped cup having a substantially hemispherically-shaped inner surface and a substantially hemispherically-shaped outer surface defining a wall therebetween, said wall having a plurality of generally circular apertures, the wall surrounding each aperture having a bevelled surface extending toward said outer surface followed by a generally cylindrical surface extending from said bevelled surface to said outer surface of said cup, said generally cylindrical surface being threaded with threads of predetermined diameter and pitch;
   a bone screw having a first screw thread having a pitch and diameter for engagement with said thread of said cylindrical surface on said cup and a second screw thread having a major diameter and a pitch greater than said predetermined diameter and pitch of said cylindrical surface; and
   a plastic insert for attachment to the inner surface of said cup.

* * * * *